US007015042B2

(12) United States Patent
Devlin, Sr.

(10) Patent No.: US 7,015,042 B2
(45) Date of Patent: Mar. 21, 2006

(54) INCREASING THROUGHPUT IN AN AUTOMATIC CLINICAL ANALYZER BY PARTITIONING ASSAYS ACCORDING TO TYPE

(75) Inventor: William Jackson Devlin, Sr., Lincoln University, PA (US)

(73) Assignee: Dade Behring Inc., Deerfield, IL (US)

( * ) Notice: Subject to any disclaimer, the term of this patent is extended or adjusted under 35 U.S.C. 154(b) by 389 days.

(21) Appl. No.: 10/151,424

(22) Filed: May 17, 2002

(65) Prior Publication Data

US 2003/0054557 A1 Mar. 20, 2003

Related U.S. Application Data

(63) Continuation-in-part of application No. 09/917,132, filed on Jul. 27, 2001, now abandoned.

(51) Int. Cl.
  *G01N 35/02* (2006.01)
(52) U.S. Cl. .............................. 436/50; 436/43; 436/47; 436/54; 436/180; 422/99; 422/100; 422/104
(58) Field of Classification Search .................. 422/64, 422/99, 100, 104; 436/43, 47, 54, 180
See application file for complete search history.

(56) References Cited

U.S. PATENT DOCUMENTS

| | | | |
|---|---|---|---|
| 4,540,549 A | 9/1985 | Manabe ....................... | 422/64 |
| 4,837,159 A | 6/1989 | Yamada ....................... | 436/45 |
| 5,434,083 A | 7/1995 | Mitsumaki et al. ........... | 436/48 |
| 5,482,861 A | 1/1996 | Clark et al. ................... | 436/48 |
| 5,575,976 A | 11/1996 | Choperena .................... | 422/64 |
| 5,576,215 A | 11/1996 | Burns et al. .................. | 436/50 |
| 5,658,799 A | 8/1997 | Choperena et al. ........... | 436/50 |
| 5,677,188 A | 10/1997 | Mitsumaki et al. | |
| 5,679,309 A | 10/1997 | Bell ............................. | 422/67 |
| 5,827,478 A * | 10/1998 | Carey et al. .................. | 422/64 |
| 5,846,491 A | 12/1998 | Choperena et al. ........... | 422/67 |
| 5,985,672 A | 11/1999 | Kegelman et al. ............ | 436/50 |

FOREIGN PATENT DOCUMENTS

| | | |
|---|---|---|
| EP | 0 316 766 | 5/1989 |
| EP | 0 355 823 | 2/1990 |

* cited by examiner

*Primary Examiner*—Jill Warden
*Assistant Examiner*—Jyoti Nagpaul
(74) *Attorney, Agent, or Firm*—Leland K. Jordan (57) ABSTRACT

A clinical analyzer where incoming samples are partitioned into groups in accord with the length of time required for the assay to be completed or in accord with the pattern of reagent addition(s) taken with length of time required for the assay to be completed. Medium length time assays are completed, removed from a reaction carousel and replaced by shorter length time assays during a single operational cycle in which longer length assays are also completed.

19 Claims, 9 Drawing Sheets

Fig. 6 note: S = stop; M = move; asp = aspirate; disp = dispense

| Operation | R1 | RX | S | RX | RX | R2 | Rd | Rd | Rd | Rd | Rd | Rd |
|---|---|---|---|---|---|---|---|---|---|---|---|---|
| Minutes | -.036 | -.006 | 0.00 | 0.66 | 1.38 | 2.10 | 3.00 | 3.66 | 6.00 | 7.26 | 9.66 | 10.86 |
| Seconds | -21.6 | -3.6 | 0.0 | 39.6 | 82.8 | 126.0 | 180.0 | 219.6 | 360.0 | 435.6 | 579.6 | 651.6 |
| Type A Assay | R1 | | S | Rd | Rd | Rd | Rf | | | | | |
| Type B Assay | R1 | | S | | | | Rd | Rd | Rf | | | |
| Type C Assay | R1 | | S | | | | Rd | Rd | Rd | Rd | Rd | Rf |

R1 = 1st Reagent Addition
S = Sample Addition
Rd = Read by Devices 70
Rf = Final Read

Fig. 7

| Event Timing | | | | | | | |
|---|---|---|---|---|---|---|---|
| T1 | TX | T0 | | | | | T2 |
| Type D | R1 | | S | | | | T2 |
| Type E | R1 | | S | | | | |
| Type F | R1 | | S | | RX | | R2 |
| Type F | R1 | RX | S | | RX | | R2 |

R1 = 1st Reagent Addition
R2 = 2nd Reagent Addition
S  = Sample Addition
RX = Variable Reagent Addition

Fig. 8

| Operation | R1 | RX | S | RX | RX | R2 | Rd | Rd | Rd | Rd | Rd | Rd |
|---|---|---|---|---|---|---|---|---|---|---|---|---|
| Minutes | -.036 | -.006 | 0.00 | 0.66 | 1.38 | 2.10 | 3.00 | 3.66 | 6.00 | 7.26 | 9.66 | 10.86 |
| Seconds | -21.6 | -3.6 | 0.0 | 39.6 | 82.8 | 126.0 | 180.0 | 219.6 | 360.0 | 435.6 | 579.6 | 651.6 |
| Type D Assay | R1 | | S | Rd | | Rd | Rf | | | | | |
| Type E Assay | R1 | | S | | | R2 | Rd | Rd | Rf | | | |
| Type F Assay | R1 | RX | S | RX | | R2 | Rd | Rd | Rd | Rd | Rd | Rf |

R1 = 1st Reagent Addition
R2 = 2nd Reagent Addition
S = Sample Addition
RX = Variable Reagent Addition(s)
Rd = Read by Devices 70
Rf = Final Read

Fig. 9

INCREASING THROUGHPUT IN AN AUTOMATIC CLINICAL ANALYZER BY PARTITIONING ASSAYS ACCORDING TO TYPE

This application is a continuation-in-part of U.S. Ser. No. 09/917,132 filed on Jul. 27, 2001, which is now abandoned.

FIELD OF THE INVENTION

The present invention relates to a method and apparatus for automatically processing a patient's biological fluids such as urine, blood serum, plasma, cerebrospinal fluid and the like. In particular, the present invention provides an improved method to process patient samples on a single analyzer adapted to perform a number of different clinical assays using different assay technologies.

BACKGROUND OF THE INVENTION

Various types of tests related to patient diagnosis and therapy can be performed by analysis assays of a sample of a patient's infections, bodily fluids or abscesses. Such patient samples are typically placed in sample vials, extracted from the vials, combined with various reagents in special reaction vessels or tubes, incubated, and analyzed to aid in treatment of the patient. In typical clinical chemical analyses, one or two assay reagents are added at separate times to a liquid sample having a known concentration, the sample-reagent combination is mixed and incubated. Interrogating measurements, turbidimetric or fluorometric or absorption readings or the like are made to ascertain endpoint or rate values from which an amount of analyte may be determined, using well-known calibration techniques.

Although various known clinical analyzers for chemical, immunochemical and biological testing of samples are available, analytical clinical technology is challenged by increasing needs for improved levels of analysis. Automated clinical analyzers improve operating efficiency by providing results more rapidly while minimizing operator or technician error. However, due to increasing demands on clinical laboratories regarding assay throughput, new assays for additional analytes, accuracy of analytical results, and low reagent consumption, there continues to be a need for improvements in the overall performance of automated clinical analyzers. In particular, sample analysis continuously needs to be more cost effective in terms of reduced testing turnaround time which is usually addressed by increasing analyzer throughput, regardless of the assay to be performed.

An important contributor to maintaining a high throughput of automatic analyzers is the ability to quickly process a plurality of samples through a variety of different assay process and signal measurement steps. If there were no premium placed on space within health care facilities, automatic clinical analyzers could be designed for high-speed throughput and reliability by simply spacing apart multiple numbers of rugged components in dedicated positions to carry out different assay technologies. This is not feasible and even further, there are different standards for evaluating the rate of throughput of an automatic clinical analyzer. A volume throughput measurement relates to how much time is required for all assays on all samples to be tested to be completed. Conversely, an assay throughput measurement relates to how much time is required for a specified assay of a specified sample to be completed. For example, in terms of volume throughput, 1000 patient samples may be completed during 4 hours but the first result may be available only 3 hours after start-up. However, in terms of assay throughput, a first assay result may be available 30 minutes after a sample is placed on an analyzer but the last result may be available only 10 hours after start-up. Such diverse throughput's are not generally acceptable to laboratory personnel and therefore automatic analyzers are required to simultaneously have a high volume processing throughput in terms of sample assays/hour as well as a fast turn-around time to the first available reportable result.

One common method of scheduling assay resources to maximize throughput is based upon the use of a predetermined fixed cycle where all assay resources in the instrument operate within a fixed length, predetermined cycle. Systems having this scheduling method have each assay resource returning to a predetermined location at the end of each cycle. Automated analyzers which use a predetermined fixed cycle method of scheduling the timing of resources also have single chronology operation. Each container of sample proceeds through each of the operational stations of the analyzer in the same order. The Stratus® II Immunoassay System is such an automated immunoassay system and is described in Volume 41 of the I. Clin. Immun. In the Stratus analyzer, a generally circular reaction carousel moves forward a fixed distance for each cycle of the system, indexing sequentially in a clockwise fashion past an incubation stage, a washing stage and a reading stage. A similar process is described in U.S. Pat. No. 5,575,976 in which each assay resource has a predetermined fixed operation window within the fixed processing cycle. Resultingly, the control for one assay resource can rely on predetermined timing of other dependent and independent assay resources. Therefore, analyte tests having variable protocols and that are processed by moving reaction vessels in different chronologies can be interleaved if their assay resource requirements do not conflict, i.e., analyte tests with shorter processing time can be entered after those with longer processing times and the shorter analyte test can finish first. This can be achieved because the means of transporting reaction vessels containing assay constituents can present reaction vessels to the necessary assay resources in whatever order is required, regardless of entry order.

U.S. Pat. No. 5,434,083 uses a rotating reaction vessel train in which an analysis time of each of the test items is set to correspond to the number of times of circulation (number of cycles) of the reaction vessels on the reaction line. A reaction vessel renew device is selectively controlled for each reaction vessel in accordance with the number of cycles. Thus, a test item which requires a short reaction time is processed in a smaller number of cycles of the reaction line and a test item which requires a long reaction time is processed in a larger number of cycles The analyzer can sequentially process a plurality of test items which require different reaction times for one sample.

U.S. Pat. No. 5,482,861 operates an automated continuous and random access analytical system capable of simultaneously effecting multiple assays of a plurality of liquid samples wherein scheduling of various assays of the plurality of liquid samples is followed by creating a unit dose and separately transferring a first liquid sample and reagents to a reaction vessel without initiation of an assay reaction sequence, followed by physical transfer of the unit dose disposable to a processing workstation, whereby a mixture of the unit dose disposable reagents and sample are achieved during incubation.

U.S. Pat. No. 5,576,215 operates a biological analyzer wherein instrument systems used to perform assays of the biological samples loaded into the analyzer are operated in accordance with a schedule developed by a scheduler routine. The scheduler routine determines interval periods between operations performed by the analyzer instrument systems on each biological sample as a function of an entered load list unless a fixed interval period between the operations is required and schedules instrument system operations and the determined interval periods. The biological system analyzer performs assays of the biological samples by operating the analyzer instrument systems in accordance with the developed schedule.

U.S. Pat. No. 5,679,309 discloses a method for controlling an analyzer including a rotatable, circular reaction carousel which has circumferentially spaced cuvettes. Each cuvette, according to the menu of the analyzer, is designated to receive a selected reagent and a selected sample for reaction and analysis and, post-analysis, be washed for re-use. A drive indexes the reaction carousel to position the cuvettes according to the menu and in proper sequence, for receipt of reagent, sample and for wash and for analysis. When photometric analysis is used, the drive operates on a sequence of a spin cycle, during which the reaction carousel is spun for photometric analysis of reacting cuvettes, and a park cycle, for a period of time for insertion of reactant, sample and/or for wash.

U.S. Pat. No. 5,846,491 increases throughput by employing an analyzer control system with means for allocating assay resources to one of a number of reaction vessels as a function of the time cycle for that vessel and transferring reaction vessels directly from one assay resource station to another according to a chronology selected from a plurality of different predetermined chronologies.

U.S. Pat. No. 5,985,672 also addresses the need for high-speed processing by employing a pre-processor for use in performing immunoassays on samples for analytes in the sample employing concentrically positioned incubating and processing carousels. A single transfer station permits reaction vessels containing sample and reagents to be moved between the carousels. The samples are separated, washed and mixed on the processing carousel and incubated on the incubating carousel thus speeding up processing throughput.

Another scheduling method used in automated analyzers does not use a fixed cycle, instead using a scheduling method referred to as "kitting." U.S. Pat. No. 6,096,561 discloses an automated continuous and random access analytical system, capable of simultaneously effecting multiple assays of a plurality of liquid samples wherein various assays are scheduled for a plurality of liquid samples. Through kitting, the system is capable of creating a unit dose by separately transferring liquid sample and reagents to a reaction vessel without initiation of an assay reaction sequence. From the kitting means, multiple, kitted unit dose disposables are transferred to a process area, where an aliquot is mixed for each independent sample with one or more liquid reagents at different times in a reaction vessel to form independent reaction mixtures. Independent scheduling of kitting and mixing is achieved during incubation of the multiple reaction mixtures, simultaneously and independently. The system is capable of performing more than one scheduled assay in any order in which a plurality of scheduled assays is presented. The incubated reaction mixtures are analyzed independently and individually by at least two assay procedures which are previously scheduled.

From this discussion of the art state in automated clinical analyzers, it may be seen that while has been considerable progress has been made toward increasing processing efficiency, there remains an unmet need for a system and apparatus that provides a high volume throughput for unpredictable combinations of different type assays, particularly those which require various lengths of time to complete an assay including incubation and final reading and/or single and multiple reagent additions. There further remains an unmet need for a system and apparatus for efficiently completing unpredictable combinations of assays which require relatively longer and relatively shorter processing times.

SUMMARY OF THE INVENTION

The principal object of the invention is to provide a method for using an automatic clinical analyzer in a manner that achieves high throughput irregardless of the mix of different assays required to be performed by the analyzer for different samples presented to the analyzer. The analyzer includes a circular rotatable assay reaction carousel for holding reaction vessels and providing stepwise movements in a constant circular direction at a constant velocity, the stepwise movements being separated by constant stationary dwell times, during which dwell time an assay device may operate on an assay mixture contained within a reaction vessel. A clinical analyzer like those on which the present invention may be performed typically has a plurality of conventional assay operation stations at which are positioned individual assay devices, such as sensors, reagent add stations, mixing stations, separation stations, and the like. In a first embodiment of the present invention, during operation of the analyzer, different incoming samples for which different assays are to be performed are partitioned into a number of separate assay groups in accord with the length of time required for the assay to be completed. Judicious partitioning of assays by time, taken with carefully designed dwell times, number of reaction vessels, and location of assay devices enables a first medium time length assay and a second shorter time length assay to be completed in less than a single operational cycle, thereby increasing the analyzer's volume throughput as compared to conventional analyzers in which a reaction mixture having been analyzed may remain on a reaction carousel for an unproductive time period of inactivity. In particular, during a single full operational cycle of the reaction carousel, medium length time assays are first completed within a number of reaction vessels; as each medium length time assays is completed, those reaction vessels are removed from the reaction carousel and are replaced by new reaction vessels in which shorter length time assays are then completed. Longer length time assays remain on the reaction carousel during a full operational cycle.

An indexing drive for the reaction carousel moves the reaction vessels in the constant direction a predetermined number of incremental steps. The reaction vessels are located in two concentric circular patterns near the circumference of the reaction carousel and are spaced apart an even number of equal separation distances. The length of the circular pattern, the separation distance, the number of reaction vessels, and the number of increments per indexing are selected so that any given reaction vessel returns to its original starting position after a fixed number of incremental steps. Thus, all reaction vessels on the reaction carousel return to their original location in a full operational cycle time, defined by the number of incremental steps multiplied by the sum of dwell time at each assay device plus the time required for a stepwise movement.

In an alternate embodiment of the invention different incoming samples for which different assays are to be performed are partitioned into a number of groups in accord with the pattern of reagent addition(s) taken with length of time required for the assay to be completed. In particular, the assays are partitioned such that those assays that can be completed by the analyzer with the addition of two reagents at a fixed time relative to sample addition and in an amount of time less than about half of the full operational cycle time are placed into a first assay grouping. Similarly, all assays that can be completed by the analyzer with the addition of only one reagent at a fixed time relative to sample addition, and in an amount of time less than the difference between full operational cycle time and time required for the first grouping of assays to be completed, are placed into a dedicated second assay grouping. Finally, all assays that require the addition of at least two reagents, one at a fixed time and the other at a variable time relative to sample addition, and essentially full operational cycle time for completion are placed into a dedicated third assay grouping. In practicing this embodiment of the present invention, during a single full operational cycle time, after the first grouping of assays are completed, the first grouping of reaction vessels are removed from the reaction carousel and are replaced by the second grouping of assays.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
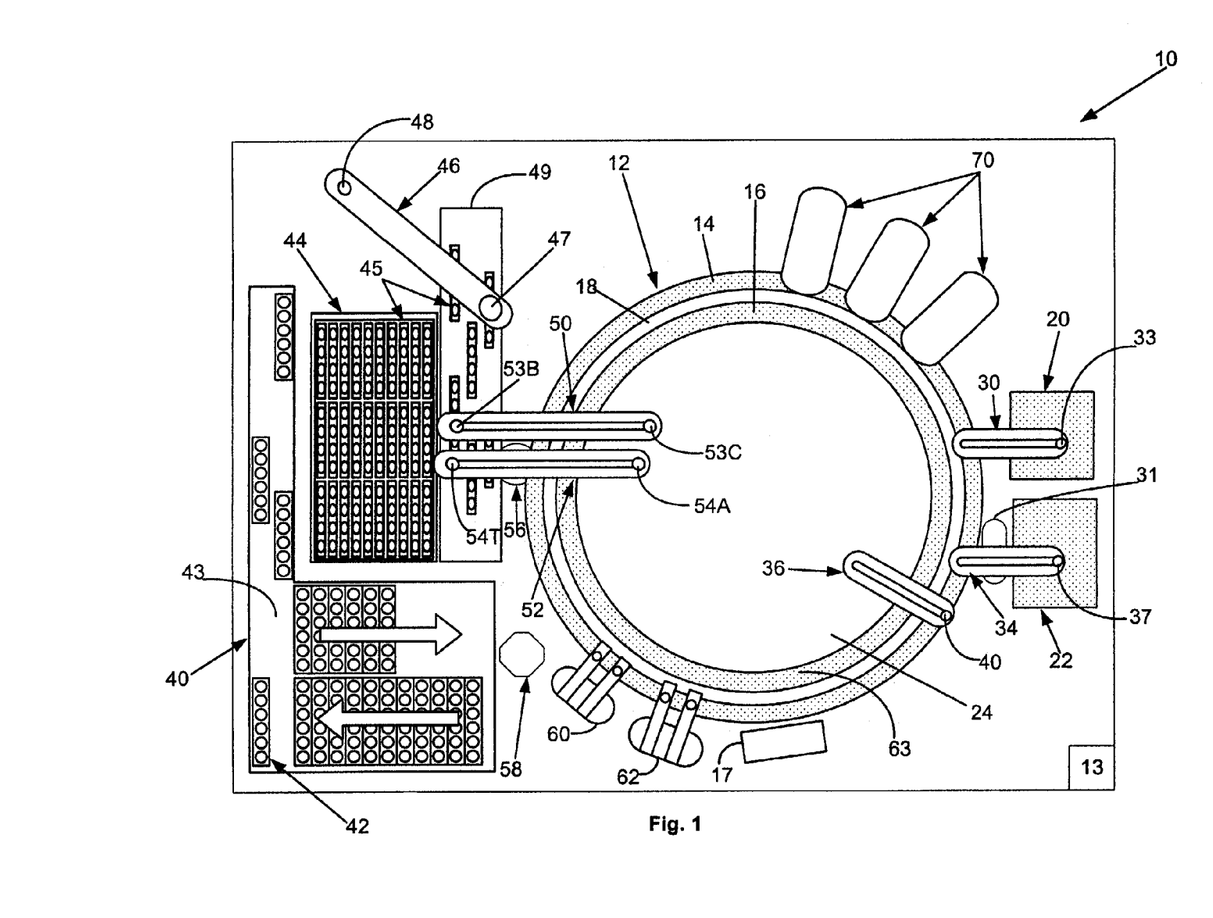
FIG. 1 is a schematic plan view of an automated analyzer in which the present invention may be used to advantage.
Figure 2:
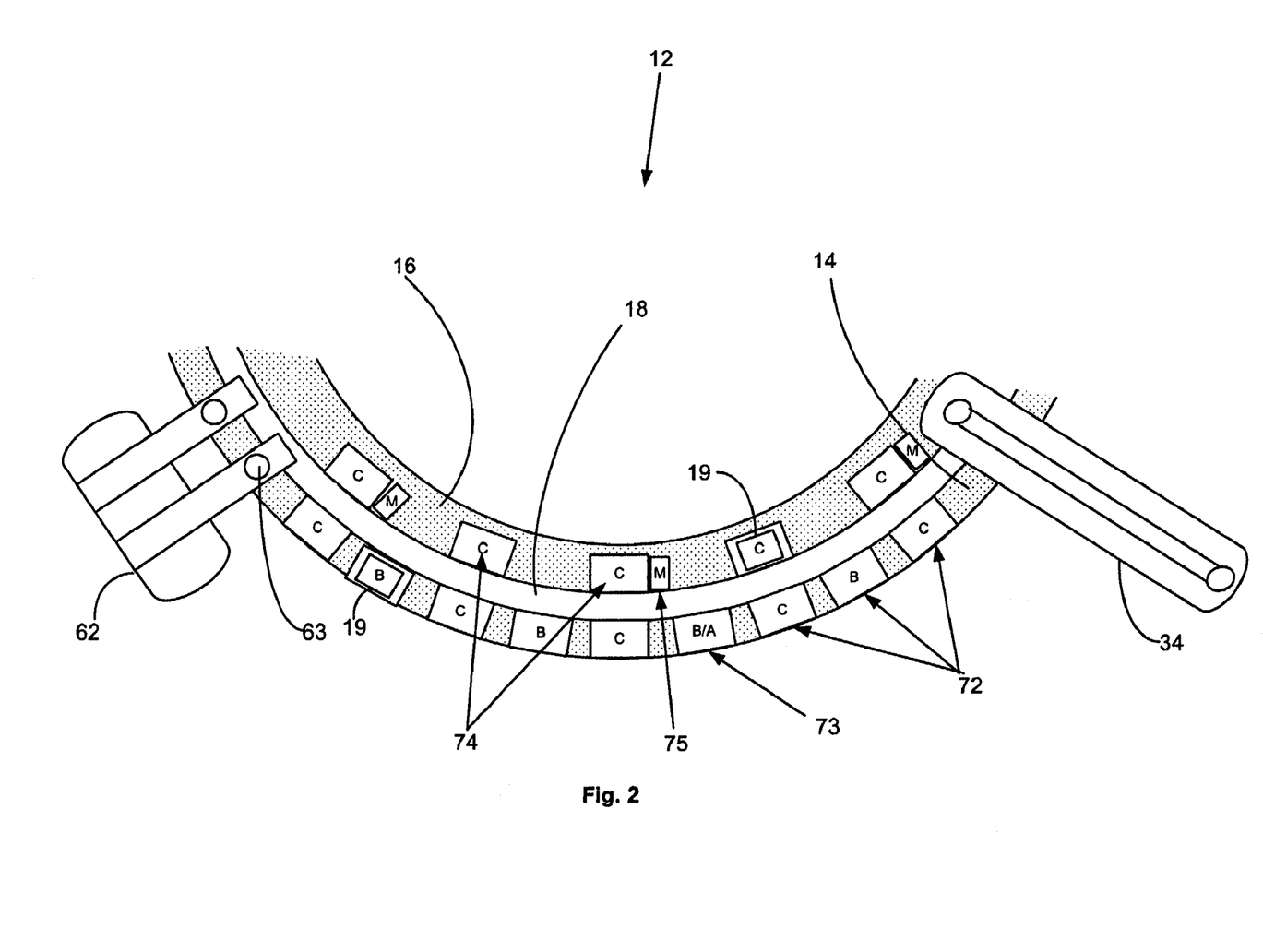
FIG. 2 is an enlarged partial schematic plan view of the automated analyzer of FIG. 1.

FIG. 1, taken with FIG. 2, shows schematically the elements of a convention automatic chemical analyzer 10 comprising a reaction carousel 12 supporting a outer cuvette circle 14 of cuvette ports 72 and 73 and an inner cuvette circle 16 of cuvette ports 74, the outer cuvette circle 14 and inner cuvette circle 16 being separated by a open groove 18. Cuvette ports 72, 73 and 74 are adapted to receive a plurality of reaction cuvettes 19 typically formed as small, flat walled, U-shaped containers with an open central reaction portion closed at the bottom and with an opening at the top of the cuvettes 19 to allow the addition of reagent and sample liquids. Reaction carousel 12 is rotatable using stepwise movements in a constant direction at a constant velocity, the stepwise movements being separated by a constant dwell time during which dwell time, carousel 12 is maintained stationary and an assay device located proximate carousel 12 may operate on an assay mixture contained within a cuvette 19.

Figure 3:
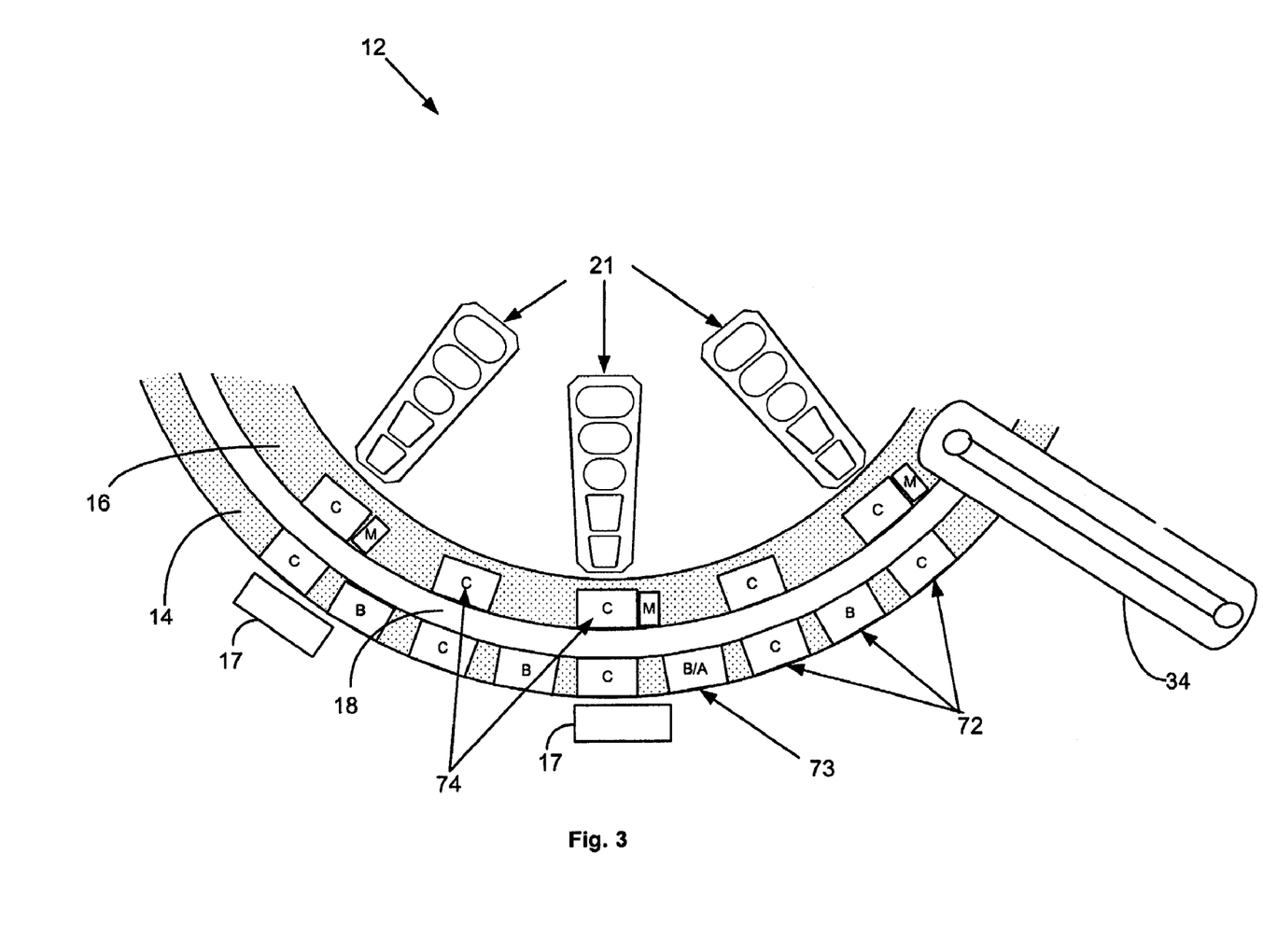
FIG. 3 is an enlarged partial schematic plan view of the automated analyzer of FIG. 1.

Three temperature-controlled reagent storage areas 20, 22 and 24 each store a plurality of reagent cartridges 21, cartridges 21, for example being a multi-compartmented reagent container like those described in U.S. Pat. No. 4,720,374, sold under the tradename FLEX(tm) cartridge by Dade Behring Inc, Deerfield, Ill., and containing reagents as necessary to perform a given assay. A selectively-opened lid (not shown) covers each of reagent storage areas 20, 22 and 24 to allow access to cartridges 21; for simplicity, only three reagent cartridges 21 are schematically illustrated in FIG. 3 as disposed beneath a cut out portion of reagent storage area 24, however similar reagent cartridges 21 are disposed within reagent storage areas 20 and 22. Shuttle means (not shown) move individual cartridges 21 to probe access ports. Storage areas 20 and 22 may be conveniently located external to the circumference of outer cuvette circle 14 and reagent storage area 24 may be conveniently located internal to the circumference of inner cuvette circle 16.

A clinical analyzer 10 like those on which the present invention may be performed has a plurality of conventional assay operation stations disposed proximate carousel 12 and at which are positioned individual computer controlled electro-mechanical devices, such as sensors, reagent add stations, mixing stations, and the like, as required to perform the myriad of actions required in well known clinical assays. Such devices and their operation are well known in the art and need not be described herein. See for example, U.S. Pat. Nos. 5,876,668, 5,575,976 and 5,482,861 and the references cited therein.

An indexing drive for the reaction carousel moves the reaction vessels in the constant direction a predetermined numbers of incremental steps. The length of the circumference of cuvette circle 14, the separation distance between cuvette ports 72, 73 and 74, the number of cuvette ports 72, 73 and 74, and the number of increments per indexing are selected so that any given cuvette ports 72, 73 or 74 returns to its original starting position after a fixed number of incremental steps. Thus, all cuvette ports 72, 73 and 74 on the reaction carousel 14 return to their original location in a full operational cycle time, hereinafter CT, which is determined by the fixed number of incremental steps multiplied by the sum of dwell time at each assay device and the time required for a stepwise movement.

A principal object of the invention is to provide a method for operating an automatic clinical analyzer in a manner that achieves high throughput irregardless of the mix of different assays required to be performed for different samples presented to the analyzer. An important feature of analyzer 10 is a unique partitioning of the assays to be performed into groups defined by the length of time required to complete those assays. To achieve these ends, a number of liquid aspiration and dispense arms 30, 34, and 36 are located proximate the reagent storage areas 20, 22 and 24 and controlled by a programmed computer 13, preferably a microprocessor based central processing unit (CPU) to control all activities of analyzer 10 according to pre-programmed software, firmware, or hardware commands or circuits. Aspiration and dispense arm 34 has an aspiration probe 37, is operable to remove reagents from cartridges 21 stored within reagent storage area 22 and to dispense aspirated reagent into cuvettes 19 for a first grouping of those assays for which final incubation and test readings can be completed in an amount of time less than about half of the full operational cycle time of carousel 12. Aspiration and dispense arm 30 similarly has an aspiration probe 33, is operable to remove reagents from cartridges 21 stored within reagent storage area 20 and to dispense aspirated reagent into cuvettes 19 for a second grouping of assays for which final incubation and test readings can be completed by the analyzer in an amount of time less than the difference between full operational cycle time of carousel 12 and the time required for the first grouping of assays to be completed. Aspiration and dispense arm 36 also has an aspiration probe 40, is operable to remove reagents from cartridges 21 stored within reagent storage area 24 and to dispense aspirated reagent into cuvettes 19 for those assays for which final incubation and test readings are completed in an amount of time less than the full operational cycle time of carousel 12.

As previously mentioned, a key feature of the operation of analyzer 10 includes partitioning assays are into a number of groups in accord with the length of time required for the assay to be completed. For the sake of description, the first grouping of assays will be called B-type assays hereinafter and consists of all those assays that require less than about one-half of the operational cycle CT of the cuvette circle 14 for completion of the full B-type assay process including reagent addition and incubation until a final reading is made. The second grouping of assays, called Type A assays, consists of all those assays that require less than about one-fourth to one-half of the operational cycle CT; that is less than the difference between the full operational cycle CT of the cuvette circle 14 and the time for Type B assays to reach completion of their respective assay processes including reagent addition and incubation until a final reading is made. The third grouping of assays, called Type C assays, consists of all assays other than Type A or Type B assays; such assays generally require more than about one-half of the operational cycle CT for completion of the full assay process including reagent addition and incubation until a final reading is made and remain on reaction carousel 12 during a full operational cycle. Such partitioning of assays by time, taken with carefully designed dwell times and total number of reaction vessels, enables one Type B assay and Type A assay to be fully completed in less than a full operational cycle, during which cycle, a single Type C will be fully completed.

FIG. 2 illustrates a useful pattern for using the cuvette ports in which ports 74 are dedicated exclusively to the use of Type C assays and are equally spaced along the circumference of cuvette circle 16 in radial alignment with alternate cuvette ports 72 equally spaced along the circumference of cuvette circle 14. Alternate ports 74 have a magnetic separation device 75 associated therewith to enable magnetic separation of a solution within a cuvette 19 positioned in such alternating ports 74. In contrast, cuvette ports 72 and 73 are useful for Type C assays, Type B assays, and A-type assays. In an advantageous embodiment, alternate cuvette ports 72 are dedicated exclusively to the use of Type C assays and the intervening cuvette ports 72 are dedicated exclusively to the use of Type B and Type A assays. For the purpose of illustration, a cuvette port 73 is marked "B/A" to indicate that a port 72 is initially used to perform a B-type assay and after that certain Type B assay is completed, a Type A assay is performed in cuvette port 73.

Cuvette load and unload stations 60 and 62 are positioned proximate outer cuvette carousel 14 and are conventionally adapted to load cuvettes 19 into cavities 72, 73 and 74 seen in FIG. 2 formed in both outer cuvette carousel 14 and inner carousel 16 using for example a translatable robotic clamp 63. Conventional sample processing devices, or stations 17 (FIG. 3), are positioned at selected circumferential locations about the reaction carousel 12 in order to access reaction vessels 19. Stations 17 are adapted to provide, among other processing steps, for mixing together of the sample liquid and the reagent liquid contained in a cuvette 19, for washing the sample liquid and the reagent liquid contained in a cuvette 19, and for magnetic separation of tagged magnetic particles from free tags or reagent liquid contained in a cuvette 19.

Incoming sample specimens to be tested are transported by a sample tube transport system 40 and inventoried within analyzer 10 inside an environmental chamber 44 as described in co-pending application Ser. No. 09/827,045 assigned to the assignee of the present invention. Specimens are typically contained in open tubes 41 supported in racks 42 and are identified by reading bar coded indicia on sample tubes 41 using a conventional bar code reader to determine, among other items, a patient's identity, the tests to be performed, if a sample aliquot is desired to be retained inside environmental chamber 44 and if so, for what period of time.

Figure 4:
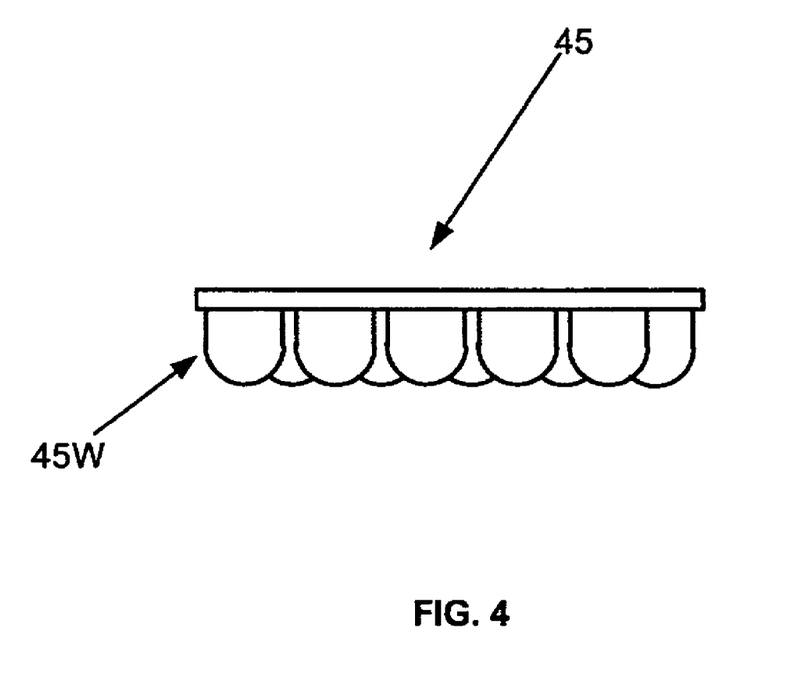
FIG. 4 is a schematic elevation view of a multi-well aliquot strip useful within the automated analyzer of FIG. 1.

A sampling arm 46 supports a conventional liquid sampling probe 47 and is mounted to a rotatable shaft 48 so that movement of sampling arm 46 describes an arc intersecting the sample tube transport system 40 and an aliquot strip transport system 49 adapted to transport aliquot strips 45, seen in FIG. 4, to a pair of conventional sample/reagent aspiration and dispense arms 50 and 52 located proximate reaction carousel 12. Sampling arm 46 is operable to aspirate liquid sample from sample tubes 41 and to dispense a sample aliquot into one or more of a plurality of wells 45W in aliquot strips 45, depending on the quantity of sample required to perform the requisite assays and to provide for a sample aliquot to be retained by analyzer 10 within environmental chamber 44. After sample has been dispensed into cuvettes, conventional transfer means move aliquot strips 45 as directed between aliquot strip transport system 49 and storage compartment 44.

Sample aspiration and dispense arms 50 and 52 are controlled by computer 13 and adapted to remove sample from aliquot strips 45 and to dispense aspirated sample into cuvettes 19 for testing. Each of the sample aspiration and dispense arms 50 and 52 comprises a pair of conventional liquid probes 53B, 53C and 54A, 54T, respectively, the probes being independently mounted and translatable upon a single translatable shaft. Probes 53B and 53C are shown in FIG. 1 in two operating positions, with one probe, 53B, adapted to remove sample from aliquot strips 45 and to dispense aspirated sample into cuvettes 15B for Type B assay testing located in outer cuvette carousel 14. Probe 53C is adapted to remove sample from aliquot strips 45 and to dispense aspirated sample into cuvettes 15C for Type C assay testing. Probe 53C is further adapted to remove liquid from special "control" containers 21 in reagent storage area 24, in the instance that a calibrated liquid solution is maintained on-board as part of routine quality assurance measures. Probes 53B, 53C, 54A, and 54T typically comprise an ultrasonic mechanism used for hydrating, aspirating, dispensing and mixing reagents. The hydrating, aspirating, dispensing and mixing mechanisms have features well known in the art and need not be described further.

Probes 54A and 54T are shown in FIG. 1 in two operating positions, with one probe, 54A, adapted to remove sample from aliquot strips 45 and to dispense aspirated sample into cuvettes 19 in ports 73 for A-type assay testing located in outer cuvette carousel 14. Probe 54T is adapted to remove sample from aliquot strips 45 and to dispense aspirated sample into a port 56 that feeds an ion-selective-electrode (ISE) test station 58 located proximate reaction carousel 12 as shown. ISE test station 58 is adapted to perform ionic analyte testing, for instance using an electrically charged or neutral ionophore dispersed in an ion selective electrode in the clinical measurement of sodium, potassium, chloride and similar ions. When such an electrode is exposed to a sample solution, an ion of interest is selectively transferred from the sample solution to the electrode. The charge associated with the ions generate a potential that can be mathematically related to the concentration or activity of the ion content in the sample.

Various other assay analyzing means 70 may be located proximate outer cuvette carousel 14 and are adapted to measure light absorbence in or emission from cuvettes 15 at various wavelengths, from which the presence of analyte in the sample liquid may be determined using well-known analytical techniques. Means 70 typically comprise conventional photometric, fluorometric or luminescent measuring devices adapted to perform an interrogating measurement at any convenient time interval during which reaction carousel 12 is stationary, as explained below.

Drive means are provided for independently rotating outer reaction carousel 12 about an axis, the drive means typically comprising gear teeth disposed on the carousel 12 and interlacing with pinion gears mounted on the shaft of a motor. The drive means may be of conventional design and are not illustrated.

Analyzer 10 is controlled by computer 13 based on software written in a machine language, like that used on the Dimension® clinical chemistry analyzer sold by Dade Behring Inc, of Deerfield, Ill., and widely used by those skilled in the art of computer-based electromechanical control programming.

Figure 5:
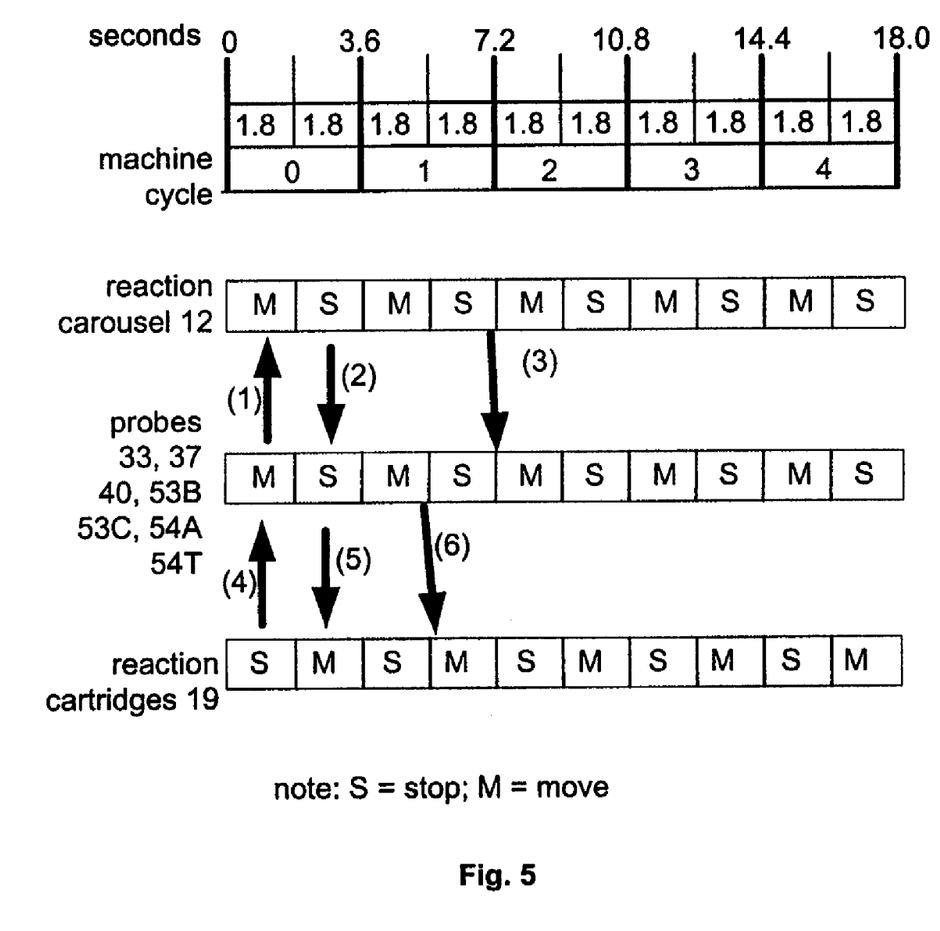
FIG. 5 is a timing illustration showing motion of elements of the automated analyzer of FIG. 1.
Figure 6:
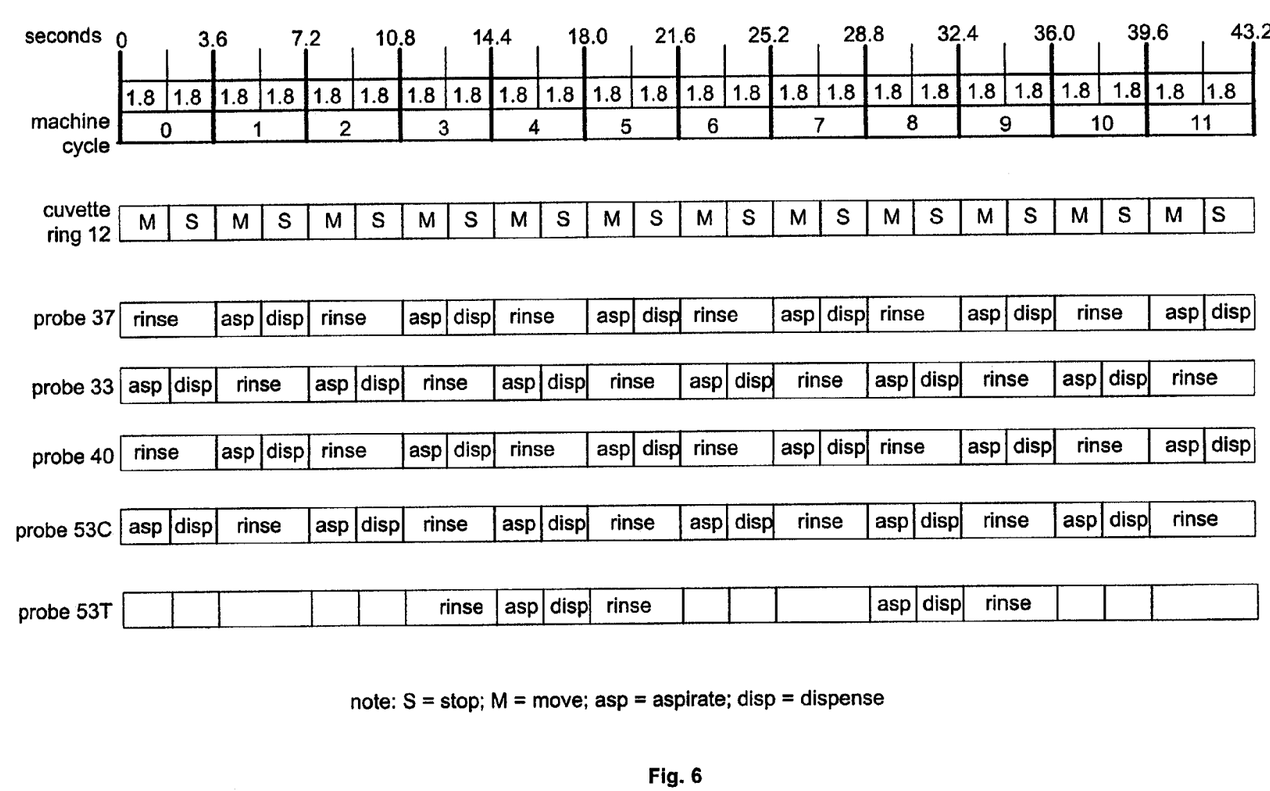
FIG. 6 is a timing illustration showing operations of devices of the automated analyzer of FIG. 1.

Important elements that must be understood in practicing the present invention include various analyzer function timings, like those shown in FIGS. 5 and 6. For the purpose of further explanation, and in an exemplary embodiment of the present invention, reaction carousel 12 comprises 184 cuvette ports 72 located in cuvette ring 14 and moves or advances step-wise in a single rotational direction (clockwise or counter-clockwise) a total of 77 cuvette positions during the initial portion of each machine cycle. Each step-wise movement of 77 cuvette positions is followed by a corresponding stationary dwell time. The combination of a step-wise movement and subsequent stationary dwell time comprise a machine cycle of 3.6 seconds and are equal in time, so that reaction carousel 12 moves step-wise for a total of 1.8 seconds and is subsequently stationary for a period of 1.8 seconds. The prime-number relationships between the numbers of 184 cuvette ports 72 and the number of 77 cuvette positions moved in each machine cycle is well known in the art (U.S. Pat. No. 5,352,612) from which it may be determined that after a total of 184 machine cycles occur, each and every cuvette port 72 is returned to its each and every original starting position, thereby defining a full carousel cycle of 184 machine cycles of duration 3.6 seconds; the full carousel cycle thus comprising 662.4 seconds or approximately 11 minutes. FIG. 5 illustrates five full machine cycles and the activities therein of reaction carousel 12, liquid aspiration and dispense probes 33, 37, 40, 53B, 53C, 54A and 54T. It is important to note that the reaction carousel 12 moves for 1.8 sec during the first half-portion of a machine cycle and remains stationary for 1.8 sec during the subsequent second half-portion of a machine cycle. Similarly, liquid aspiration and dispense probes 33, 37, 40, 53B, 53C, 54A and 54T are independently moveable for 1.8 sec during the first half-portion of a machine cycle and remain stationary for 1.8 sec during the subsequent second half-portion of a machine cycle during which second half-portion of a machine cycle reagents may be dispersed into cuvettes 19 in cuvette ports 72. On the other hand, shuttle means to position cartridges 19 beneath liquid aspiration and dispense probes 33, 37, 40 remains stationary for 1.8 sec during the first half-portion of a machine cycle during which first half-portion of a machine cycle reagents may be aspirated from reagent cartridges 21 in reagent storage areas 20, 22 and 24 and are independently moveable as required for 1.8 sec during the subsequent second half-portion of a machine cycle. Three other arrows indicate that: (4) reagent containers 19 remain stationary when liquid aspiration and dispense probes 33, 37, 40, 53B, 53C, 54A and 54T are in an aspiration mode; (5) that reagent containers 19 move when liquid aspiration and dispense probes 33, 37, 40, 53B, 53C, 54A and 54T are in a dispense mode and reaction carousel 12 remains stationary; and (6) that reagent containers 19 initiate movement immediately after liquid aspiration and dispense probes 33, 37, 40, 53B, 53C, 54A and 54T are stationary in a dispense mode.

Three arrows indicate that: (1) liquid aspiration and dispense probes 33, 37, 40, 53B, 53C, 54A and 54T move when reaction carousel 12 moves; (2) that liquid aspiration and dispense probes 33, 37, 40, 53B, 53C, 54A and 54T remain stationary in a dispense mode when reaction carousel 12 is stopped; and (3) that liquid aspiration and dispense probes 33, 37, 40, 53B, 53C, 54A and 54T initiate movement immediately after reaction carousel 12 stops.

FIG. 6 illustrates how representative ones of the probes 33, 37, 40, 53C and 53T are operable during different machine cycles. Each machine cycles comprises either a cleansing rinse action or a combined aspiration and dispensing action. Cleansing rinse actions typically comprise use of a conventional rinse station 31 provided in the active pathway of a probe like 37. about 3.0 sec out of a total 3.6 sec machine cycle; aspiration and dispensing actions each separately comprise about 1.5 sec for a total of about 3.0 sec out of a total 3.6 sec machine cycle. It is important to independent operation of the six different when aspiration and dispense arms 30, 32, 34, 36, 50 and 50 that all probes 33, 37, 40, 53A, 53B, 53C, and 54T are similarly adapted so that their respective independent aspiration and dispensing actions each separately comprise about 1.5 sec within a machine cycle. Probe 53T which is adapted to aspirate and dispense sample into the port for IMT testing remains inactive as indicated in FIG. 6, for a period of time after a cleansing rinse because of the time required for a single channel IMT test device to operate on a single sample. Since IMT testing are low demand assays, a single IMT test device is typically adequate, however, multiple channel IMT testing devices may be employed if increased throughput were required to satisfy a clinic's demands. The additional aspirations and dispensings would occur during the previously idle time.

Figure 7:
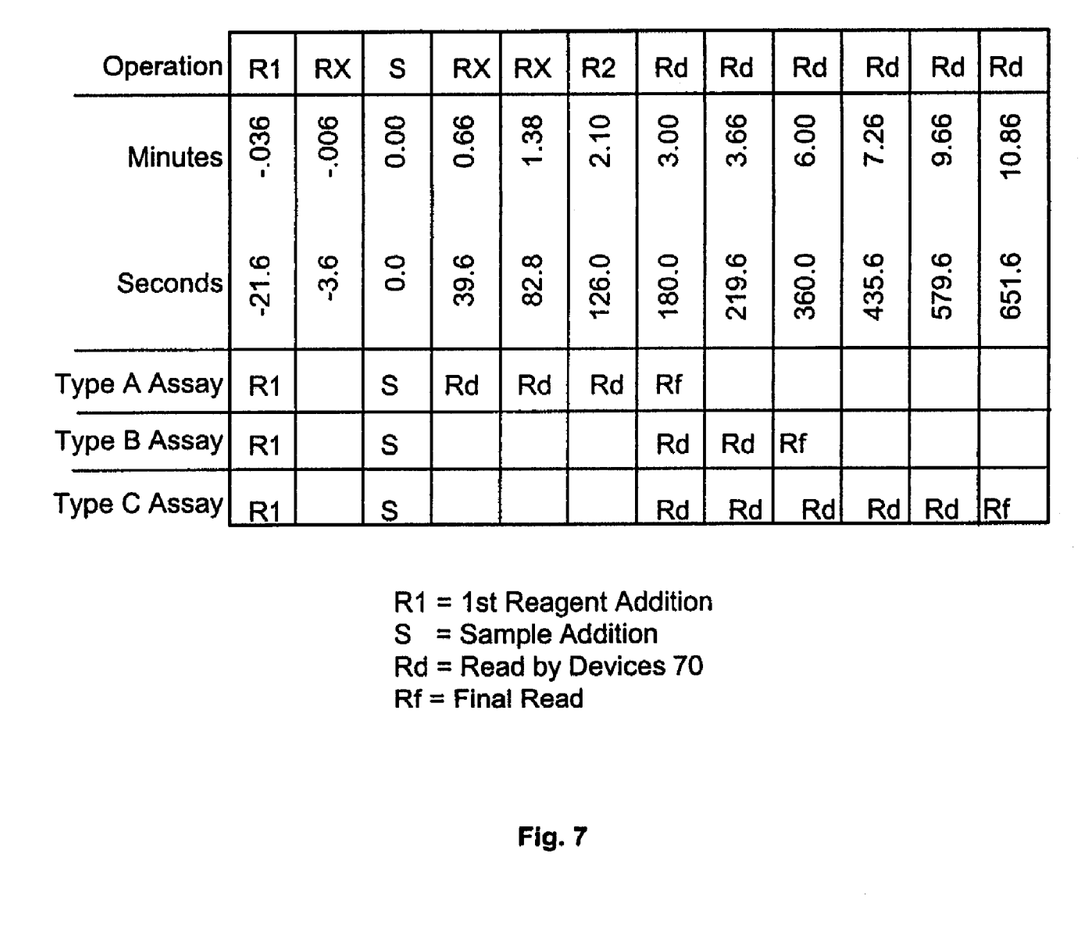
FIG. 7 illustrates an embodiment of partitioning assay types by assay time in accord with the present invention.

FIG. 7 illustrates the aforementioned partitioning of assays capable of being performed by analyzer 10 into three time-dependent assay-categories in accord with the present invention. As a matter of convention, time t=0.0 seconds is defined as the moment of sample dispensing into a test cuvette 19; for the sake of simplicity, all three types of assays are shown as having a single reagent addition R1 at a fixed time before sample addition. FIG. 7 shows how all Type A assays are required to have an assay format in which a final reading, indicated by Rf, is completed within about 180 seconds after sample addition for this embodiment in which reaction carousel 12 comprises 184 cuvette ports 72 and moves or advances step-wise in a counter-clockwise direction a total of 77 cuvette positions during a machine comprising movement during 1.8 seconds followed by a stationary period of 1.8 seconds. It should be appreciated that the final reading time requirement for Type A assays could be adjusted for analyzer 10 layouts different than the embodiment being described. What is important to the partitioning of assays into Type A assays is that the final assay reading conducted by testing devices 70 be completed in an amount of time less than about one-fourth or one-third of a complete operational cycle time, or 180–220 seconds. At any time, indicated by Rd, during the assays, a reaction vessel reading or analysis may be made by any of the devices 70.

Type B assays are generally more complex than Type A assays and are required to have an assay format in which a final reading is completed within about 360 seconds after sample addition for this embodiment in which reaction carousel 12 comprises 184 cuvette ports 72 and moves or advances step-wise in a counter-clockwise direction a total of 77 cuvette positions during a machine comprising movement during 1.8 seconds followed by a stationary period of 1.8 seconds. It should be appreciated that the reading time requirement for Type B assays could be adjusted for analyzer 10 layouts different than the embodiment described. What is important to the partitioning of assays into Type B assays is that the final assay reading conducted by testing devices 70 be completed in an amount of time approximately equal to about one-half of a complete operational cycle time or about 360 seconds.

Type C assays are generally more complex than Type A and Type B assays and are required to have an assay format in which a final reading is completed within about 600 seconds after sample addition for this embodiment in which reaction carousel 12 comprises 184 cuvette ports 72 and moves or advances step-wise in a counter-clockwise direction a total of 77 cuvette positions during a machine comprising movement during 1.8 seconds followed by a stationary period of 1.8 seconds.

Table 1 contains a listing of typical clinical and immunoassays for various Type A, B and C analytes along with timing details for various reagent additions and device operations. In Table 1:

Albumin, blood urea nitrogen, calcium, creatinine, gamma glutamyl transferase, glucose, lactate dehydrogenase, methadone, salicylate and total $CO_2$ readily fall into the category Type A Assays with final read at <180 seconds;

Alkaline phosphatase, C-reactive protein, creatine kinase, direct bilirubin, gentamicin, prealbumin, pseudocholinesterase, phenytoin, phosphorous, and triglyceride readily fall into the category Type B Assays with a final read at <360 seconds; and, Ammonia, cholesterol HDL, Complement 3, digitoxin, lactic acid, phenobarbitol, prostatic acid phosphatase, total bilirubin, and transferrin fall into the category of Type C Assays with a final read at >360 seconds.

TABLE 1

| Assay | TYPE | T1 | S | T2 | Tx | Rd1 | Rd2 | Rf-Final |
|---|---|---|---|---|---|---|---|---|
| Albumin | A | −57.6 | 0.0 | n/a | | | | 124.7 |
| Alkaline Phosphatase | B | −57.6 | 0.0 | 220 | | 284.5 | | 342.1 |
| Ammonia | C | −57.6 | 0.0 | | 205.6 | 241.3 | | 450.1 |
| Blood Urea Nitrogen | A | −57.6 | 0.0 | n/a | | | | 124.7 |
| Calcium | A | −57.6 | 0.0 | n/a | | −27.9 | | 67.1 |
| Cholesterol (HDL) | C | −57.6 | 0.0 | | 147.5 | 141.1 | | 442.9 |
| Cholesterol (Total) | A | −57.6 | 0.0 | n/a | | | | 378.1 |
| C-Reactive Protein | B | −57.6 | 0.0 | N/a | | −22.3 | 31.1 | 228.3 |
| Complement 3 | C | −57.6 | 0.0 | 220 | | 44.1 | 189.5 | 430.1 |
| Creatine Kinase | B | −57.6 | 0.0 | n/a | | 226.9 | | 284.5 |
| Creatinine | A | −57.6 | 0.0 | n/a | | 29.7 | | 59.9 |
| Digitoxin | C | −57.6 | 0.0 | | 248.0 | | 426.9 | 450.0 |
| Direct Bilirubin | B | −57.6 | 0.0 | 220 | | 182.3 | | 277.3 |
| Gamma Glutamyl Transferase | A | −57.6 | 0.0 | n/a | | | | 110.3 |
| Gentamicin | B | −57.6 | 0.0 | | 175.3 | 44.9 | 58.9 | 359.9 |
| Glucose | A | −57.6 | 0.0 | n/a | | −27.9 | 103.1 | 178.3 |
| Lactate Dehydrogenase | A | −57.6 | 0.0 | n/a | | | | 124.7 |
| Lactic Acid | C | −57.6 | 0.0 | | 68.8 | 36.9 | | 658.9 |
| Methadone | A | −57.6 | 0.0 | | 119 | 150.9 | | 179.7 |
| Phenobarbital | C | −57.6 | 0.0 | 220 | | 29.7 | 182.3 | 442.9 |
| Phenytoin | B | −57.6 | 0.0 | | 67.4 | 44.1 | | 255.7 |
| Phosphorous | B | −57.6 | 0.0 | 220 | | 182.3 | | 342.1 |
| Prealbumin | B | −57.6 | 0.0 | | | −17.3 | 29.9 | 297.9 |
| Prostatic Acid Phosphatase | C | −57.6 | 0.0 | | 463.6 | | | 514.9 |
| Pseudocholinesterase | B | −57.6 | 0.0 | 220 | | 255.7 | | 284.5 |
| Total Bilirubin | C | −57.6 | 0.0 | 220 | | 182.3 | 342.1 | 450.1 |
| Total CO2 | A | −57.6 | 0.0 | n/a | | −40.9 | 20 | 59.9 |
| Salicylate | A | −57.6 | 0.0 | | 54.4 | 36.9 | | 88.7 |
| Transferrin | C | −57.6 | 0.0 | 220 | | 44.1 | 189.5 | 430.1 |
| Triglyceride | B | −57.6 | 0.0 | 220 | | | 255.7 | 284.5 |
| Valproic Acid | C | −57.6 | 0.0 | n/a | | 74.9 | 212.9 | 422.8 |

As a matter of further explanation, a simplified operation of analyzer 10 with one each of a Type C, Type B and Type A assay will be described. In this alternate embodiment, reagent storage area 20 comprises reagent containers for assay types A, while reagent storage area 22 comprises reagent containers for assay types B, and while reagent storage area 24 comprises reagent containers 21 for assay types C as well as special reagent-style containers that contain liquid solutions of known analyte concentrations for quality control management.

Prior to the loading of cuvettes 19 with sample contained within aliquot wells 45 and to be tested using a Type C assay, a first reagent R1 is aspirated by probe 40 from an appropriate compartment of a reagent container within reagent storage area 24 and selected for the Type C assay to be performed and is deposited into a cuvette 19 in a cuvette port 72 or 74 at a time T1. At time T0, samples for which Type C assays have been ordered are aspirated by probe 53C and deposited within the cuvette 19 in cuvette port 74.

In a similar manner, prior to the loading of cuvettes 19 with sample contained within aliquot wells 45 and to be tested using a Type B assay, a first reagent R1 is aspirated by probe 37 from an appropriate compartment of a reagent container within reagent storage area 22 and selected for the Type B assay to be performed and is deposited into a cuvette 19 in a cuvette port 72 at a time T1. At time T0, samples for which Type B assays have been ordered are aspirated by probe 53B and deposited within the cuvette 19 in cuvette port 72.

After the cuvettes 72 and 74 are loaded with the just described reagents and samples, reaction carousel 12 continues the aforedescribed stepwise counter-clockwise movement during which machine cycles, various conventional assay devices operate upon the mixture within the cuvettes 19 in cuvette ports 72 and 74 according to the appropriate assay protocols.

Because Type B assays have been partitioned in a manner such that all such assays are completed in less than one-half of the time required for reaction carousel 12 to complete a full operational cycle time CT, cuvettes 19 containing completed Type B assays may be removed from cuvette ports 72 in the outer cuvette circle 14 of the reaction carousel 12 by unload device 62. Unused cuvettes 19 are then loaded into the emptied cuvette ports 72 by load device 60 and are made available for a second Type B assay or for a Type A assay, depending on the mixture of assay types required to be performed by analyzer 10. Prior to the loading of cuvettes 19 with sample contained within aliquot wells 45 and to be tested using a Type A assay, a first reagent R1 is aspirated by probe 33 from an appropriate compartment of a reagent container within reagent storage area 20 and selected for the Type A assay to be performed and is deposited into a cuvette 19 in a cuvette port 73, identified as B/A in FIG. 2 at a time T1. At time T0, samples for which Type A assays have been ordered are aspirated by probe 54A and deposited within the cuvette 19 in cuvette port 73. Reaction carousel 12 continues the aforedescribed stepwise counter-clockwise movement during which machine cycles, various conventional assay devices 17 operate upon the mixture within the cuvettes 19 in cuvette ports 73 containing Type A assays and in cuvette ports 74 containing Type C assays according to the appropriate assay protocols until the reaction carousel 12 completes a complete a full operational cycle time CT and both the Type A assays and Type C assays are completed.

In comparison with conventional analyzers in which, using the just described process, completed Type B assays would remain on reaction carousel 12 for a full operational cycle time CT and hinder analyzer throughput, the present invention provides an alternate method whereby one medium time length assay, described herein as a Type B assay, and one shorter time length assay, described herein as a Type A assay, are both completed during the same operational cycle time CT as required for one longer time length assay, described herein as a Type C assay, is completed, thereby enhancing analyzer throughput.

Alternately, in the event that a cuvette port 74 is vacant because there are no samples available for which Type C assays have been ordered, and samples for either Type A assays or Type B assays have been ordered are available and have not been completed, then the either Type A assays or Type B assays may be placed in to a cuvette 19 in cuvette port 74 and completed during a first partial cycle time CT, thereby further contributing to an increased throughput of analyzer 10. In the instance that cuvette port 74 is filled with a Type A assay, and if there are still no samples available for which Type C assays have been ordered, and if samples for additional Type A assays are available and have not been completed, then an additional Type A assay may be placed in to a cuvette 19 in cuvette port 74 and completed during a second partial cycle time CT, even further contributing to an increased throughput of analyzer 10.

Figure 8:
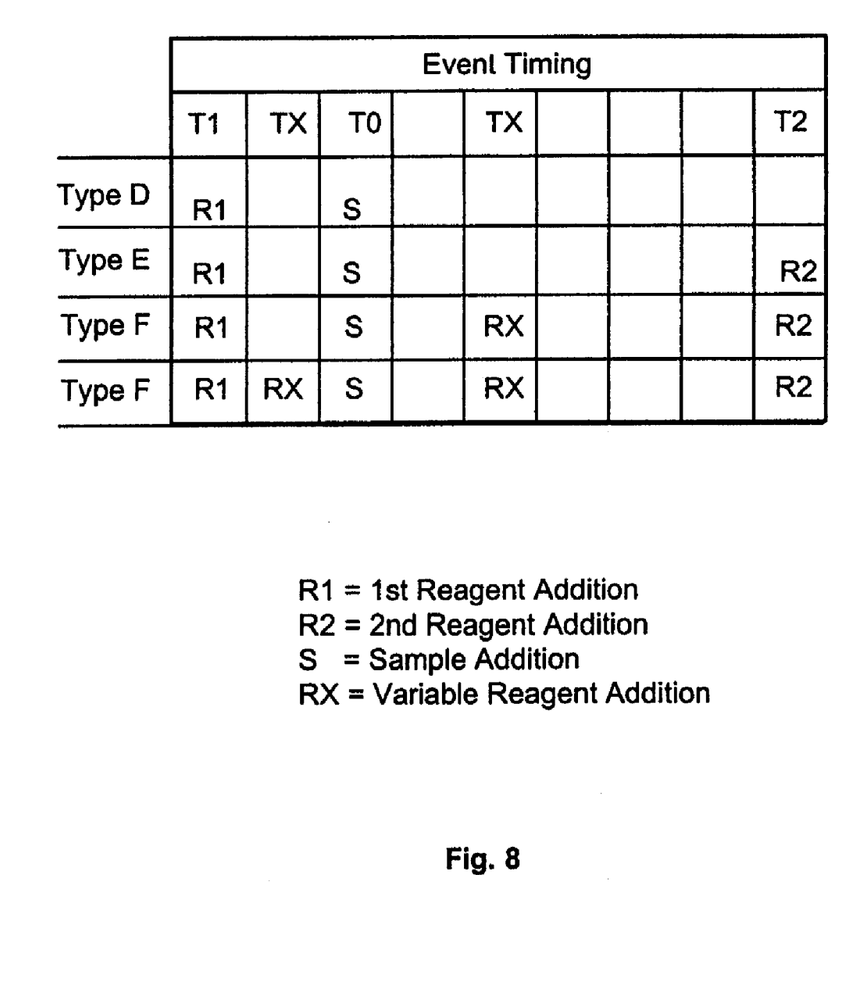
FIG. 8 is an illustration of partitioning assay types by reagent additions in accord with the present invention; and, FIG. 9 illustrates an alternate embodiment of partitioning assay types by assay time and by reagent additions in accord with the present invention.

FIG. 8 defines another partitioning of assays into Type D, E, and F assays depending upon the reagent additions, indicated by R1, R2, and RX, are required to perform the assay and in which the symbol "R1" indicates an initial reagent taken from reagent supply 20 for a Type D assay, taken from reagent supply 22 for a Type E assay, taken from reagent supply 24 for a Type F assay and dispensed into a test cuvette at a fixed time T1 before sample addition. The letter "S" indicates a sample addition that may be achieved at time T0 by probe 54A for Type D assays, by probe 53B for Type E assays and by probe 53C for Type F assays from one or more of the a plurality of wells 45W in aliquot strips 45, depending on the quantity of sample required to perform the requisite assay. Similarly, the symbol "R2" indicates an subsequent reagent taken from reagent supply 22 for a Type E assay, or taken from reagent supply 24 for a Type F assay, and that is dispensed into test cuvette 19 at a fixed time T2 after sample addition S. Finally, the symbol "RX" indicates a reagent addition(s) that may be taken from reagent supply 24 for a Type F assay, and that is dispensed into test cuvette 19 at variable times TX before and after sample addition S.

Figure 9:
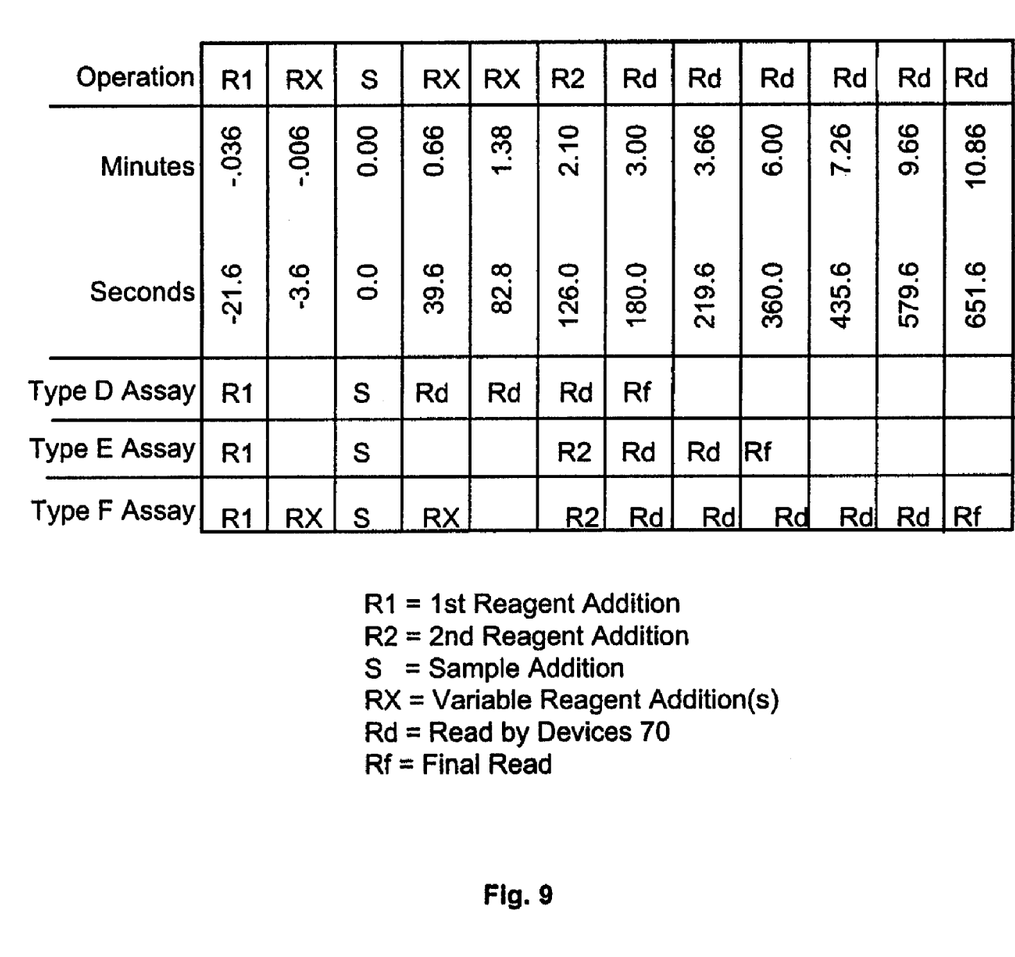

FIG. 9 illustrates an alternate embodiment of the present invention in which assays capable of being performed by analyzer 10 are partitioned into three categories that are both time-dependent and assay-format-dependent like shown in FIGS. 7 and 8. As a matter of convention, time T=0.0 seconds is defined as the moment of sample dispensing into a test cuvette 19. FIG. 9 shows how all Type D assays are defined as having an assay format in which a single reagent is dispensed into a test cuvette at a fixed time T1 before sample addition and in which a final reading is completed within about one-fourth to one-third of an operational cycle; i.e., within about 180–220 seconds after sample addition S for the analyzer embodiment in which reaction carousel 12 comprises 184 cuvette ports 72 and advances step-wise in a counter-clockwise direction a total of 77 cuvette positions during a machine cycle comprising movement during 1.8 seconds followed by a stationary period of 1.8 seconds. It should be appreciated that the absolute reading time requirement for Type D assays could be adjusted for analyzer 10 layouts different than the embodiment described. What is important to this alternate partitioning of assays into Type D assays is that the final assay reading conducted by testing devices 70 be completed in an amount of time less than about one-fourth or one-third of a complete operational cycle time.

Type E assays are generally more complex than Type D assays and are defined as having an assay format in which one reagent is dispensed into a test cuvette at a fixed time T1 before sample addition, in which a second reagent is dispensed into a test cuvette at a fixed time T2 after sample addition S, and in which a final reading is completed within about one-half of an operational cycle; i.e., within about 360 seconds after sample addition S for the analyzer configuration described above. It should be appreciated that the reading time requirement for Type E assays could be adjusted for analyzer 10 layouts different than the embodiment described. What is important to the partitioning of assays into Type E assays is that the final assay reading conducted by testing devices 70 be completed in an amount of time approximately equal to about one-half of a complete operational cycle time.

Type F assays are generally more complex than Type D and Type E assays and are defined as having an assay format in which in which one reagent is dispensed into a test cuvette at a fixed time T1 before sample addition, in which a second reagent is dispensed into a test cuvette at a fixed time T2 after sample addition S, in which additional reagent addition(s) may be made at variable time(s) before or after sample addition S and in which a final reading is completed within an operational cycle for the analyzer configuration described above.

As a matter of further explanation, a simplified operation of analyzer 10 with one each of a Type F, Type E and Type D assay will be described. In this alternate embodiment, reagent storage area 20 comprises reagent containers for assay Types D, while reagent storage area 22 comprises reagent containers for assay types E, and while reagent storage area 24 comprises reagent containers 21 for assay types FF.

Prior to the loading of cuvettes 19 with sample contained within aliquot wells 45 and to be tested using a Type F assay, a first reagent R1 is aspirated by probe 40 from an appropriate compartment of a reagent container within reagent storage area 24 and selected for the Type F assay to be performed and is deposited into a cuvette 19 in a cuvette port 72 or 74 at a time T1. Subsequently and optionally, a second reagent RX may be aspirated by probe 40 from another compartment of the reagent container selected for the assay to be performed and is deposited into a cuvette 19 in a cuvette port 72 or 74 at any time TX. At time T0, samples for which Type F assays have been ordered are aspirated by probe 53C and deposited within the cuvette 19 in cuvette port 74. To facilitate this operational flexibility, FIG. 3 shows that cuvette ports 72 and 74 are radially aligned within an inner cuvette circle 16 and outer cuvette circle 14, respectively. Additional reagent(s) RX may be aspirated by probe 40 from another compartment of the reagent container selected for the Type F assay to be performed and deposited into a cuvette 19 in a cuvette port 72 at time(s) TX after time T0 and before time T3.

In a similar manner, prior to the loading of cuvettes 19 with sample contained within aliquot wells 45 and to be tested using a Type E assay, a first reagent R1 is aspirated by probe 37 from an appropriate compartment of a reagent container within reagent storage area 22 and selected for the Type E assay to be performed and is deposited into a cuvette 19 in a cuvette port 72 at a time T1. At time T0, samples for which Type E assays have been ordered are aspirated by probe 53B and deposited within the cuvette 19 in cuvette port 72. Subsequently, a second reagent R2 may be aspirated by probe 37 from another compartment of the reagent container selected for the Type E assay to be performed and is deposited into a cuvette 19 in a cuvette port 72 at a time T2.

After the cuvettes 72 and 74 are loaded with the just described reagents and samples, reaction carousel 12 continues the aforedescribed stepwise counter-clockwise movement during which machine cycles, various conventional assay devices operate upon the mixture within the cuvettes 19 in cuvette ports 72 and 74 according to the appropriate assay protocols. As indicated in FIG. 8, in the case of Type F assays, additional reagents RX may be aspirated by probe 40 from another compartment of the reagent container selected for the Type F assay to be performed and deposited into a cuvette 19 in a cuvette port 72 at a times TX before and after time T0 and before time T2.

Because Type E assays have been partitioned in a manner such that all such assays are completed in less than one-half of the time required for reaction carousel 12 to complete a full operational cycle time CT, cuvettes 19 containing completed Type E assays may be removed from cuvette ports 72 in the outer cuvette circle 14 of the reaction carousel 12 by unload device 62. Unused cuvettes 19 are then loaded into the emptied cuvette ports 72 by load device 60 and are made available for a second Type E assay or for a Type D assay, depending on the mixture of assay types required to be performed by analyzer 10. Prior to the loading of cuvettes 19 with sample contained within aliquot wells 45 and to be tested using a Type D assay, a first reagent R1 is aspirated by probe 33 from an appropriate compartment of a reagent container within reagent storage area 20 and selected for the Type D assay to be performed and is deposited into a cuvette 19 in a cuvette port 73, identified as B/A in FIG. 2 at a time T1. At time T0, samples for which Type D assays have been ordered are aspirated by probe 54A and deposited within the cuvette 19 in cuvette port 73. Reaction carousel 12 continues the aforedescribed stepwise counter-clockwise movement during which machine cycles, various conventional assay devices 17 operate upon the mixture within the cuvettes 19 in cuvette ports 73 containing Type D assays and in cuvette ports 74 containing Type F assays according to the appropriate assay protocols until the reaction carousel 12 completes a complete a full operational cycle time CT and both the Type D assays and Type F assays are completed.

In comparison with conventional analyzers in which, using the just described process, completed Type E assays would remain on reaction carousel 12 for a full operational cycle time CT and hinder analyzer throughput, the present invention provides an alternate method whereby one medium time length assay having two reagent additions, described herein as a Type E assay, and one shorter time length assay having one reagent addition, described herein as a Type D assay, are both completed during the same operational cycle time CT as required for one longer time length assay having multiple reagent additions, described herein as a Type F assay, is completed, thereby enhancing analyzer throughput.

Alternately, in the event that a cuvette port 74 is vacant because there are no samples available for which Type F assays have been ordered, and samples for either Type D assays or Type E assays have been ordered are available and have not been completed, then the either Type D assays or Type E assays may be placed in to a cuvette 19 in cuvette port 74 and completed during a first partial cycle time CT, thereby further contributing to an increased throughput of analyzer 10. In the instance that cuvette port 74 is filled with a Type D assay, and if there are still no samples available for which Type F assays have been ordered, and if samples for additional Type D assays are available and have not been completed, then an additional Type D assay may be placed in to a cuvette 19 in cuvette port 74 and completed during a second partial cycle time CT, even further contributing to an increased throughput of analyzer 10.

Table 2 contains a listing of typical clinical and immunoassays for various Type D, E and F analytes along with timing details for various reagent additions and device operations. In Table 1:

Albumin, blood urea nitrogen, calcium, creatinine, gamma glutamyl transferase, glucose, lactate dehydrogenase, and total $CO_2$ readily fall into the category Type D Assays with a single reagent add at fixed T1 and a final read at <180 seconds;

Alkaline phosphatase, C-reactive protein, creatine kinase, direct bilirubin, prealbumin, pseudocholinesterase, phosphorous, and triglyceride readily fall into the category Type E Assays with single reagent adds at fixed times T1 and T2 and a final read at <360 seconds;

Complement 3, phenobarbitol, total bilirubin, and transferrin fall into the category of Type F Assays with single reagent adds at fixed times T1 and T2 and a final read at >360 seconds; and, Ammonia, cholesterol HDL, digitoxin, gentamicin, lactic acid, methadonee, prostatic acid phosphatase, phenytoin, and salicylate fall into the category of Type F Assays with at lest one reagent add at variable time TX regardless of the amount of time to a final read.

Complement 3, fall into the category of Type F Assays even though they have a single reagent add at fixed time T1 because they do not meet the final read time requirements of Type D or E assays.

Accommodating a myriad of such assays within a single analyzer is a task regularly encountered within the art and need not be described herein. It is sufficient that the teachings of the present invention, that partitioning assays by type and providing reagent storage and access probes dedicated to the different types, need only be presented to such artisans so that an previously unachievable increase in analyzer throughput be achieved. It is to be understood that the embodiments of the invention disclosed herein are illustrative of the principles of the invention and that other modifications may be employed which are still within the scope of the invention. For instance, cuvette circle 14 may have a larger or smaller number of cuvette ports 72, machine cycle times may be appropriately adjusted, additional reagent supply sources may be provided, and the like without affecting the partitioned of incoming samples into groups by the length of time required for the assay to be fully completed so that medium length time assays are completed, removed from a reaction carousel and replaced by shorter length time assays during a single operational cycle in which cycle longer length assays are also completed. Alternately, incoming samples may be partitioned into groups in accord with the pattern of reagent addition(s) taken with by the length of time required for the assay to be fully completed so that medium length time assays having two fixed time reagent additions are completed, removed from a reaction carousel and replaced by shorter length time assays having one fixed time reagent addition during a single operational cycle in which cycle longer length assays having variable time reagent additions are also completed. For these reasons,

TABLE 2

| Assay | TYPE | T1 | S | T2 | Tx | Rd1 | Rd2 | Rf-Final |
|---|---|---|---|---|---|---|---|---|
| Albumin | D | −57.6 | 0.0 | n/a | | | | 124.7 |
| Alkaline Phosphatase | E | −57.6 | 0.0 | 220 | | 284.5 | | 342.1 |
| Ammonia | F | −57.6 | 0.0 | | 205.6 | 241.3 | | 450.1 |
| Blood Urea Nitrogen | D | −57.6 | 0.0 | n/a | | | | 124.7 |
| Calcium | D | −57.6 | 0.0 | n/a | | −27.9 | | 67.1 |
| Cholesterol (HDL) | F | −57.6 | 0.0 | | 147.5 | 141.1 | | 442.9 |
| Cholesterol (Total) | D | −57.6 | 0.0 | n/a | | | | 378.1 |
| C-Reactive Protein | E | −57.6 | 0.0 | N/a | | −22.3 | 31.1 | 228.3 |
| Complement 3 | F | −57.6 | 0.0 | 220 | | 44.1 | 189.5 | 430.1 |
| Creatine Kinase | E | −57.6 | 0.0 | n/a | | 226.9 | | 284.5 |
| Creatinine | D | −57.6 | 0.0 | n/a | | 29.7 | | 59.9 |
| Digitoxin | F | −57.6 | 0.0 | | 248.0 | | 426.9 | 450.0 |
| Direct Bilirubin | E | −57.6 | 0.0 | 220 | | 182.3 | | 277.3 |
| Gamma Glutamyl Transferase | D | −57.6 | 0.0 | n/a | | | | 110.3 |
| Gentamicin | F | −57.6 | 0.0 | | 175.3 | 44.9 | 58.9 | 389.9 |
| Glucose | D | −57.6 | 0.0 | n/a | | −27.9 | 103.1 | 178.3 |
| Lactate Dehydrogenase | D | −57.6 | 0.0 | n/a | | | | 124.7 |
| Lactic Acid | F | −57.6 | 0.0 | | 68.8 | 36.9 | | 658.9 |
| Methadone | F | −57.6 | 0.0 | | 119 | 150.9 | | 179.7 |
| Phenobarbital | F | −57.6 | 0.0 | 220 | | 29.7 | 182.3 | 442.9 |
| Phenytoin | F | −57.6 | 0.0 | | 67.4 | 44.1 | | 255.7 |
| Phosphorous | E | −57.6 | 0.0 | 220 | | 182.3 | | 342.1 |
| Prealbumin | E | −57.6 | 0.0 | | | −17.3 | 29.9 | 297.9 |
| Prostatic Acid Phosphatase | F | −57.6 | 0.0 | | 463.6 | | | 514.9 |
| Pseudocholinesterase | E | −57.6 | 0.0 | 220 | | 255.7 | | 284.5 |
| Total Bilirubin | F | −57.6 | 0.0 | 220 | | 182.3 | 342.1 | 450.1 |
| Total CO2 | D | −57.6 | 0.0 | n/a | | −40.9 | 20 | 59.9 |
| Salicylate | F | −57.6 | 0.0 | | 54.4 | 36.9 | | 88.7 |
| Transferrin | F | −57.6 | 0.0 | 220 | | 44.1 | 189.5 | 430.1 |
| Triglyceride | E | −57.6 | 0.0 | 220 | | | 255.7 | 284.5 |
| Valproic Acid | F | −57.6 | 0.0 | n/a | | 74.9 | 212.9 | 422.8 | the present invention is not limited to those embodiments precisely shown and described in the specification but only by the following claims.

I claim:

1. A method of operating an analyzer adapted to perform numerous different assays on a plurality of different samples and assay reagents contained in different reaction cuvettes during a single operational cycle time, the method comprising:

partitioning the cuvettes into three separate groups based on the assays being performed and the length of time required to complete the assays;

operating the analyzer for an single operational cycle time, during which single cycle time all of the assays are completed; wherein said operating comprises performing a first assay and a third assay on first and third groups of cuvettes, respectively:

removing a first group of said three groups of cuvettes from the analyzer during said operational cycle while continuing to perform said third assay;

replacing said first group with a second group of said three groups of cuvettes during said operational cycle; and, leaving said third group of cuvettes on the analyzer throughout the single operational cycle time.

2. The method of claim 1 wherein said first assay being performed in said first group of cuvettes comprises assays with a length of time less than about one-half of the operational cycle time.

3. The method of claim 1 wherein said second assay being performed in said second group of cuvettes comprises assays with a length of time less than about one-third of the operational cycle time.

4. The method of claim 1 wherein said third assay being performed in said third group of cuvettes comprises all assays except those in said first group and said second group.

5. The method of claim 1 wherein said single operational cycle time comprises a stepwise rotation with intervening stationary dwell times of a circular carousel adapted to support the reaction cuvettes.

6. The method of claim 5 wherein the stepwise rotation is a constant number of movements a constant length in a constant direction.

7. A method of operating an analyzer adapted to perform numerous different assays on a plurality of different samples and assay reagents contained in different reaction cuvettes during a single operational cycle time, the method comprising:

partitioning the cuvettes into three separate groups based on the assays being performed and the length of time and pattern of reagent addition required to complete the assays;

operating the analyzer for an single operational cycle time, during which single cycle time all of the assays are completed; wherein said operating comprises performing a first assay and a third assay on first and third groups of cuvettes, respectively:

removing a first group of said three groups of cuvettes from the analyzer during said operational cycle;

replacing said first group with a second group of said three groups of cuvettes during said operational cycle; and, leaving said third group of cuvettes on the analyzer throughout the single operational cycle time.

8. The method of claim 7 wherein said first assay being performed in said first group of cuvettes comprises assays with a length of time less than about one-half of the operational cycle time and two reagents are required.

9. The method of claim 7 wherein said second assay being performed in said second group of cuvettes comprises assays with a length of time less than about one-third of the operational cycle time and no more than one reagent is required.

10. The method of claim 7 wherein said third assay being performed in said third group of cuvettes comprises all assays except those in said first group and said second group.

11. The method of claim 7 wherein said single operational cycle time comprises a stepwise rotation a constant number of movements a constant length in a constant direction with intervening stationary dwell times of a circular carousel adapted to support the reaction cuvettes.

12. The method of claim 8 wherein the two reagents are placed into the reaction cuvette before and after sample is placed therein.

13. The method of claim 8 wherein the single reagent is placed into the reaction cuvette before sample is placed therein.

14. The method of claim 10 wherein multiple reagents may be placed into the reaction cuvette before and after sample is placed therein.

15. The method of claim 12 wherein the two reagents are placed into the reaction cuvette at a first predetermined time before sample is placed therein and at a second predetermined time after sample is placed therein.

16. The method of claim 13 wherein the single reagent is placed into the reaction cuvette at a first predetermined time before sample is placed therein.

17. The method of claim 14 wherein the multiple reagents are placed into the reaction cuvette at predetermined times before and after sample is placed therein.

18. The method of claim 1 wherein said third group comprises only assays in said first group and said second group.

19. The method of claim 7 wherein said third group comprises only assays in said first group and said second group.

* * * * *